United States Patent
Ward et al.

(10) Patent No.: US 10,466,155 B2
(45) Date of Patent: Nov. 5, 2019

(54) SYSTEM AND METHOD FOR PROVIDING STABLE FLUID FLOW

(71) Applicant: LIFE TECHNOLOGIES CORPORATION, Carlsbad, CA (US)

(72) Inventors: Michael Ward, Eugene, OR (US); Jason Malkin, Eugene, OR (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 15/373,722

(22) Filed: Dec. 9, 2016

(65) Prior Publication Data
US 2017/0191922 A1    Jul. 6, 2017

Related U.S. Application Data (60) Provisional application No. 62/376,974, filed on Aug. 19, 2016, provisional application No. 62/272,799, filed on Dec. 30, 2015.

(51) Int. Cl.
*G01N 15/14* (2006.01)
*F04B 11/00* (2006.01)
(Continued)

(52) U.S. Cl.
CPC .......... *G01N 15/1404* (2013.01); *F04B 11/00* (2013.01); *F04B 13/00* (2013.01); *F04B 23/04* (2013.01); *F04B 49/065* (2013.01); *F04C 2/08* (2013.01); *F04C 15/0049* (2013.01); *G05D 7/0682* (2013.01); *F04B 2205/05* (2013.01); *F04B 2205/09* (2013.01); *F04C 28/02* (2013.01); *F04C 2270/145* (2013.01); *F04C 2270/185* (2013.01); *F04C 2270/205* (2013.01); *F04C 2270/215* (2013.01); *F04C 2270/44* (2013.01); *F04C 2270/80* (2013.01);
(Continued)

(58) Field of Classification Search
CPC .... G01N 15/1404; G01N 15/14; G01N 15/10; G01N 15/00; G01N 33/5308; G01N 33/53; G01N 33/50; G01N 33/48; G01N 33/00; F04B 11/00; F04B 23/04; F04B 23/00
USPC .... 422/505, 504, 502, 501, 500, 50; 436/52, 436/43
See application file for complete search history.

(56) References Cited

U.S. PATENT DOCUMENTS

| | | | |
|---|---|---|---|
| 4,510,397 A * | 4/1985 | Schroeder, Jr. ...... | G05D 7/0676 290/42 |
| 5,410,403 A | 4/1995 | Wells | |

(Continued)

FOREIGN PATENT DOCUMENTS

| | | |
|---|---|---|
| CN | 103837462 | 6/2014 |
| WO | WO-2015/121402 | 8/2015 |

OTHER PUBLICATIONS

PCT/US2016/065734, "International Search Report dated", Mar. 22, 2017, 3 Pages.

*Primary Examiner* — Christine T Mui
(74) *Attorney, Agent, or Firm* — BakerHostetler (57) ABSTRACT

An embodiment of a system with a minute measure of pulsatility in a flow of a fluid is described that comprises a first pump configured to flow the fluid to a junction at a first flow rate that comprises a measure of pulsatility; and a second pump configured to flow a portion of the fluid from the junction at a second flow rate that is less than the first flow rate to produce a flow of the fluid at a third flow rate from the junction with a minute measure of pulsatility.

24 Claims, 4 Drawing Sheets

(51) Int. Cl.
*F04B 23/04* (2006.01)
*G05D 7/06* (2006.01)
*F04B 13/00* (2006.01)
*F04B 49/06* (2006.01)
*F04C 2/08* (2006.01)
*F04C 15/00* (2006.01)
*G01N 15/10* (2006.01)
*G01N 33/48* (2006.01)
*F04C 28/02* (2006.01)

(52) U.S. Cl.
CPC ...... *F04C 2270/86* (2013.01); *F04C 2270/90* (2013.01); *G01N 2015/1409* (2013.01)

(56) References Cited

U.S. PATENT DOCUMENTS

| | | |
|---|---|---|
| 2009/0293910 A1 | 12/2009 | Ball et al. |
| 2015/0300940 A1* | 10/2015 | Bair .................. G01N 15/1404 73/863.03 |
| 2015/0330385 A1* | 11/2015 | Lofstrom ................ F04B 43/12 417/53 |

* cited by examiner

SYSTEM AND METHOD FOR PROVIDING STABLE FLUID FLOW

The present application claims the benefit of and priority to U.S. Patent Application 62/376,974 (filed on Aug. 19, 2016) and to U.S. Patent Application 62/272,799 (filed on Dec. 30, 2015), the entireties of which applications are incorporated herein by reference for any and all purposes.

FIELD OF THE INVENTION

The invention relates to Flow Cytometry, pumps, and methods for their use.

BACKGROUND OF THE INVENTION

Flow cytometers are capable of rapid and efficient analysis (e.g. "high-throughput" analysis) of particles flowing in a stream of liquid to provide real time identification of individual particles that is useful in a large number of applications. Many embodiments of flow cytometer use what is referred to as a "sheath fluid" that surrounds and aligns the particles into single file in what may be referred to as a "core diameter" of the flow profile so that they pass through a detection region in a serial fashion. Alternatively, some embodiments of flow cytometer include a single flow profile with channels having a dimension that is substantially similar in size to the dimensions of the particles allowing the particles to easily pass in single file but preventing multiple particles from passing the detector simultaneously. Particles may include cells, single molecules, droplets of fluid immiscible with the fluid composition of the stream, etc.

Flow cytometer embodiments are available to process sample streams at high flow rates (e.g. ≥10 m/s) for high speed applications and slow flow rates (e.g. ≤10 mm/s) for slow speed applications. While high flow rate flow cytometers are common, slow flow rate flow cytometers are less common and are less reliable at delivering a stable, slow sheath flow rate. The problems are typically rooted in pump and fluidic channel systems that are not well suited to both high and low flow rate throughput. The problems of delivering stable sheath flow rate can be even more difficult for flow cytometry methods that use viscous sheath fluids such as oil.

Embodiments of a flow cytometer commonly use "pressure reservoirs" and "regulators" to drive the flow of sheath fluid, which can be made stable but require careful control over temperature and viscosity of the fluids in order to maintain stability of the flow rate. In practice such systems are limited to a small dynamic range of flow rate and are generally restricted to providing either a fast or a slow sheath flow rate but not both. For example, gravimetric reservoirs have been used to produce very stable slow flow rates but are not generally practical for high flow rate systems.

Volumetric delivery methods are also used, embodiments of which may include syringe pumps and/or peristaltic pumps which are typically more robust with respect to fluid temperature and viscosity differences but are limited in dynamic range and are subject to significant pulsatility. Peristaltic pumps in particular are naturally pulsatile and must be used in conjunction with pulse dampening if any level of acceptable stability in flow rate is to be achieved. Syringe pumps may propagate larger pulse waves due to low stepper motor revolution count and large fluid volume displaced per step. Syringe wear, pump wear and fluid containing salt or particles can induce syringe stiction further exacerbating pulsatility of flow. Additionally, analysis is limited by syringe volume and must be paused for refilling. Choice of syringe size is often a compromise between the greater relative pulsation due to larger displacement volume and stiction inherent in large syringes and the higher frequency of filling required for small syringes. Examples of syringe pump pulsatility are described by Li et al. in Lab Chip. 2014 Feb. 21; 14(4):744-9, titled "Syringe-pump-induced fluctuation in all-aqueous microfluidic system implications for flow rate accuracy", which is hereby incorporated by reference herein in its entirety for all purposes.

Acquiring precise quantitative data in flow cytometry embodiments depend on stable flow rate for sheath flow that deliver particles with consistent velocity and position through the detection region of the flow cytometer. For example, it is particularly important to have a stable flow rate for sheath flow in embodiments of a flow cytometer with more than one spatially separated laser. Variations in particle flow velocity result in differences in transit time of individual particles from laser to laser, and these variations limit the number of events per second that the flow cytometer can accurately record. As the variation in particle flow velocity increases, the likelihood that the flow cytometer introduces error or even misses data from transiting particles increases.

Therefore, it is highly desirable to have flow cytometer embodiments capable of providing a stable flow at both fast and slow flow rates to provide reliable operation for a wide range of applications.

SUMMARY

Systems, methods, and products to address these and other needs are described herein with respect to illustrative, non-limiting, implementations. Various alternatives, modifications and equivalents are possible.

An embodiment of a system with a minute measure of pulsatility in a flow of a fluid is described that comprises a first pump configured to flow the fluid to a junction at a first flow rate that comprises a measure of pulsatility; and a second pump configured to flow a portion of the fluid from the junction at a second flow rate that is less than the first flow rate to produce a flow of the fluid at a third flow rate from the junction with a minute measure of pulsatility.

The above embodiments and implementations are not necessarily inclusive or exclusive of each other and may be combined in any manner that is non-conflicting and otherwise possible, whether they are presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 120 appears first in FIG. 1). All of these conventions, however, are intended to be typical or illustrative, rather than limiting.

FIGS. 3A and 3B are simplified graphical representations of measured pulsatility using 4 laser sources at a 1 m/s flow rate; and.

DETAILED DESCRIPTION OF EMBODIMENTS

As will be described in greater detail below, embodiments of the described invention include a flow cytometer instrument configured to provide a stable flow at both fast and slow flow rates. More specifically, the flow cytometer comprises a plurality of pumps that provide fluid flows comprising a minute measure of pulsatility and increase the dynamic range of flow rate. Also, some embodiments of the described invention may include one or more pressure sensors positionally arranged to provide differential measurements of input and output flow pressures associated with a flow cell.

Figure 1:
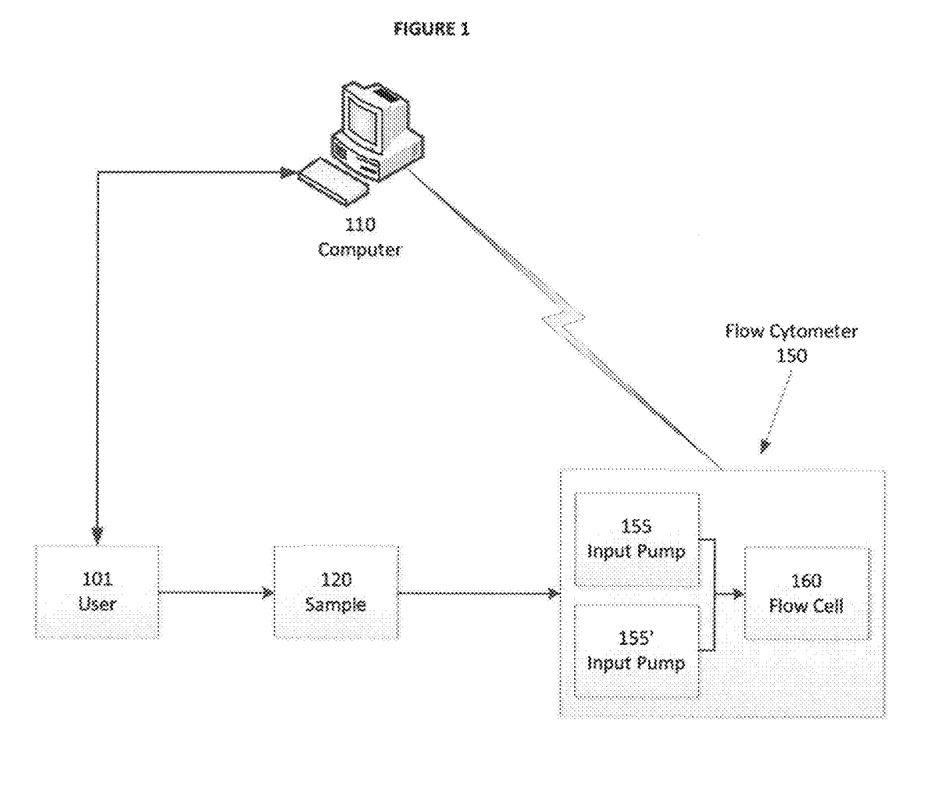
FIG. 1 is a simplified graphical representation of one embodiment of a flow cytometer instrument comprising a plurality of input pumps.

FIG. 1 provides a simplified illustrative example of flow cytometer 150 comprising input pump 155 and input pump 155' in fluid communication with flow cell 160. FIG. 1 also illustrates user 101 capable of interacting with computer 110 and sample 120, as well as a network connection between computer 110 and flow cytometer 150.

Flow cytometer 150 may include any type of flow cytometer used for slow and/or fast flow rate applications. For example an embodiment of flow cytometer may include the ATTUNE® NxT flow cytometer available from Thermo Fisher Scientific. Embodiments of flow cytometer 150 typically detect one or more measurable signals associated with a sample that include, but are not limited to, fluorescent labels, semiconductor nanocrystals (e.g. sometimes referred to as Quantum Dots) or other labeling technology known in the art. In some or all of the described embodiments, flow cytometer 150 includes one or more sources of excitation light and one more detectors enabled to detect light emissions from the samples as they pass through a detection zone in flow cell 160 that may include a channel, chamber, well, or other type of region where detection of signals can be acquired. For example, some embodiments of flow cytometer 150 may include different configurations of sources of excitation light that comprise between 1-4 laser sources each capable of providing excitation light for a variety of different fluorophores. In the present example the excitation spectra of the different laser sources do not overlap, or alternatively in some embodiments a degree of overlap may be desirable. Also, the laser sources may include a selection of excitation wavelengths comprising 405nm (e.g. violet), 488nm (e.g. blue), 561nm (e.g. yellow), and 637nm (e.g. red).

Further, embodiments of flow cytometer 150 include controller elements as well as fluidic or microfluidic components including tubes, channels, valves, pumps, flow dampeners, etc. Also, embodiments of flow cytometer 150 typically utilize fluids compatible with the application that may include aqueous fluids of various compositions, oils, or other fluid. The fluids may also contain one or more additives that enhance properties of the fluid, or improve performance in embodiments of flow cytometer 150 that may include surfactants, particles, etc. Also, in the described embodiments different fluids or fluid types may be used for the sheath portion of a flow and the core diameter portion of a flow (e.g. a sheath flow may include an oil that substantially surrounds a core diameter portion of a flow of an aqueous fluid).

Sample 120 may include any type of sample capable of being analyzed by flow cytometer 150 that includes solid particles, cells, beads, immiscible droplets, molecules, etc. As described above, sample 120 may be suspended in a fluid (e.g. in core diameter portion of a flow or a single flow) and flowed in channels of flow cytometer 150.

Computer 110 may include any type of computer platform such as a workstation, a personal computer, a tablet, a "smart phone", a server, or any other present or future computer. Computers typically include known components such as a processor, an operating system, system memory, memory storage devices, input-output controllers, input-output devices, and display devices.

In some embodiments, computer 110 may employ a computer program product comprising a computer usable medium having control logic (computer software program, including program code) stored therein. The control logic, when executed by a processor, causes the processor to perform some or all of the functions described herein. In other embodiments, some functions are implemented primarily in hardware using, for example, a hardware state machine. Implementation of the hardware state machine so as to perform the functions described herein will be apparent to those skilled in the relevant arts. Also in the same or other embodiments, computer 110 may employ an internet client that may include specialized software applications enabled to access remote information via a network. A network may include one or more of the many various types of networks well known to those of ordinary skill in the art. For example, a network may include a local or wide area network that employs what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

As described above, embodiments of the invention include a flow cytometer instrument configured to provide a stable flow at both fast and slow flow rates. More specifically, the flow cytometer comprises a plurality of pumps that operate in a mode that provides a fluid flow that comprises a minute measure of pulsatility at low flow rates as well as a mode that increases the dynamic range of flow rate also with a minute measure of pulsatility at the high flow rates. In the embodiments described herein the modes are not mutually exclusive of each other.

The term "pulsatility" as used herein generally refers to a measure of variation of flow rate that can be determined by measuring the differences in time between a plurality of individual particles that travel from a first point of interrogation to a second point of interrogation. The total sum of the measured distribution of arrival times of individual particles at the second point of interrogation minus the distribution of arrival times of the particles at the first point of interrogation represents the pulsatility of the flow rate. Typically, a uniform non-pulsatile flow will produce a small degree of variation, whereas a non-uniform pulsatile flow will produce a high degree of variation. In some embodiments the measure of variation can be expressed as pulse frequency (e.g. fpulse) and determined using the following equation:

$$fpulse = \frac{4*\text{flow\_rate}}{\text{volume\_displaced}*\text{step\_count}}$$

In the equation given above, the "volume_displaced" value refers to the volume displaced by the pump in 1 revolution or "step".

Additional examples of pulsatility determination are described in U.S. patent application Ser. No. 14/612,820, titled "Systems and Methods for Diagnosing a Fluidics System and Determining Data Processing Settings for a Flow Cytometer", filed Feb. 3, 2015, which is hereby incorporated by reference herein in its entirety for all purposes.

Many types of pump are generally known in the flow cytometry art for pumping fluids which are enabled to provide an accurate flow rate at either fast flow or slow flow rates. One type of pump that is particularly useful for many flow cytometry applications includes what is referred to as a "gear pump" that employs one or more gears to pump fluids by displacement of the fluid. Embodiments of gear pump have a variety of characteristics that can be varied to match the desired application which include the size of the gear, number and dimension of teeth, as well as rate and direction of rotation of the gears. It will also be appreciated that the gears can be constructed from a variety of different materials that may be selected to be compatible with the desired application (e.g. fluoropolymers, ceramics, metal alloys, PEEK, tungsten carbide). For example, some embodiments include gears constructed with relatively large number of small teeth dimensioned to produce a relatively smooth flow rate (e.g. increase in tooth dimension typically increases pulsatility). It will be appreciated, however, that even gear pumps with small teeth exhibit levels of pulsatility in the flow rate that are particularly evident at low rates of revolution of the gears that produce slow flow rates. In the present example a gear pump may include an inner tooth count of 6 and an outer tooth count of 7 for embodiments having an outside dimension of the outer rotor of about 3 mm and an outside dimension of the inner rotor of about 4 mm that produces about 1.5 µl fluid volume per revolution. For example, for slow flow rate cytometry applications a single gear pump is inadequate for delivery of a stable flow rate required, due to the pulsatility of the flow rate.

As described above, embodiments of gear pump are highly adjustable and capable of pumping fluids in forward and reverse directions across a range of flow rates. The range of gear pump embodiments is limited by the output per revolution of the pump and by the precision of speed control possible for the pump. For example, the MZR 2521 pump from HNP Mikrosysteme GmbH provides about 1.5 µl fluid volume per revolution output and a flow rate comprising a range of about 0.15-9 ml/min (at a range of about 100-6000 Revolutions Per Minute (e.g. RPM)). It will be appreciated that there is an inverse relationship regarding the speed that a gear pump runs at to the level of pulsatility. In other words as the RPM of a gear pump increase the level of pulsatility decreases. Thus, gear pumps run in a state at high RPM have a low pulsatility and precise differential control of multiple gear pumps run at a high RPM state can provide a slow flow rate output with low pulsatility. For example, a first pump may be run to provide flow in a first direction at 1000 rpm and a second pump may be run at 990 RPM in a second direction that reduces the fluid flow from the first direction and thus the overall fluid flow rate of the first flow is lower. In the present example, a high RPM state may include a range of about 900-6000 RPM.

Further, unlike pressure reservoirs, syringe pumps, or peristaltic pumps, gear pumps are well suited to the pumping of oils. This makes it possible to use the same or similar gear pump architectures to run an oil sheath cytometer which enable a wide range of dimension of the core diameter portion of flows (e.g. a minimum core diameter of 1 µm). Also, gear pumps are generally less expensive than other positive displacement pump types such as high precision, low flow pump types. For example, gear pump architectures can provide a range of core diameter flow dimension that depends, at least in part on the viscosity of the oil. Those of ordinary skill in the related art understand that oils can include a range of viscosity from a degree of viscosity that is less than the viscosity of water to a degree of viscosity that significantly greater than that of water.

Continuing with the above example, the upper end of the range of flow rate output of a system comprising multiple pumps is dictated by the maximum flow rate of the pump type (e.g. assuming all pumps are of the same type) times the number of pumps in the circuit when running all pumps in the forward direction. For the MZR 2521 this rate is 9 ml/min, so 2 pumps used together are capable of an 18 ml/min maximum flow rate, which could be the range of flow rate required for a high event rate flow cytometry application. It will be appreciated that many types of gear pump are available with different flow rate characteristics and that the present example should not be considered as limiting.

In the embodiments described herein two or more input pumps are employed in different modes of operation to support both fast and slow flow rate applications to provide various functions that includes a mode that provides a fluid flow that comprises a minute measure of pulsatility at low flow rates as well as a mode to produce a wide dynamic range of flow rate. It will also be appreciated that while different modes of operation are described, some capabilities described as operating in different modes may function, at least in part, in substantially the same mode and thus each description of mode should not be considered as limiting.

Figure 2:
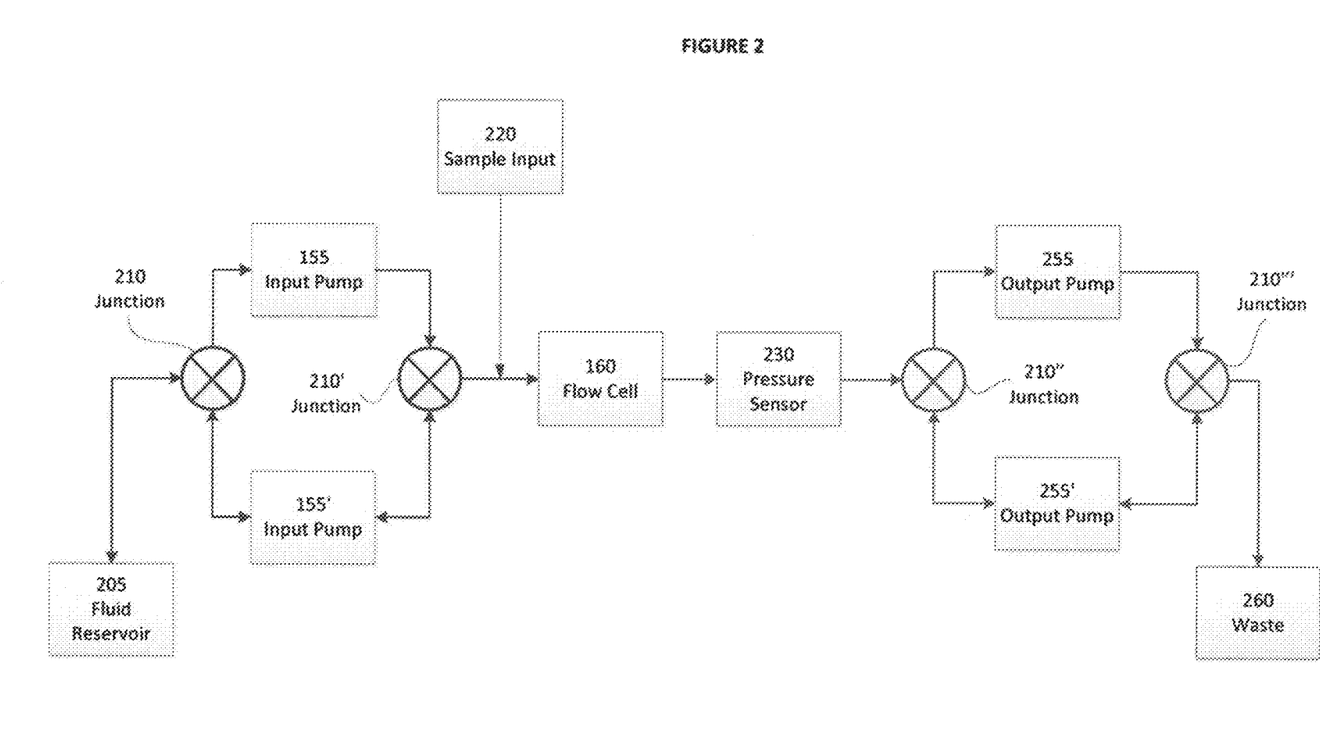
FIG. 2 is a simplified graphical representation of one embodiment of an arrangement of the input pumps of FIG. 1 and a pressure sensor.

FIG. 2, illustrates an example of inlet pumps 155 and 155' configured to operate in different modes of operation (e.g. illustrated by the bidirectional arrows), one such mode configured to provide a flow rate comprising a minute measure of pulsatility in the flow of fluid that arrives at and enters a detection region associated with flow cell 160. For example, pump 155 pumps a fluid from fluid reservoir 205 in a direction towards junction 210' and pump 155' pumps the fluid in an opposite direction from junction 210' towards junction 210 at a slightly lower flow rate than the flow rate provided by pump 155. Some embodiments of pump 155/155' provide a range of flow are from 0.5 ml/min up to 9 ml/min, however it is appreciated that the flow rate provided can vary depending on the selection of pump. This results in a low total forward flow rate from junction 210' to flow cell 160 due to the subtraction of the pump 155' flow rate from the pump 155 flow rate. The result is a stable slow sheath flow rate comprising a minute measure of pulsatility that can be easily and precisely adjusted by varying the speed of pumps 155 and 155'.

Figure 3A:
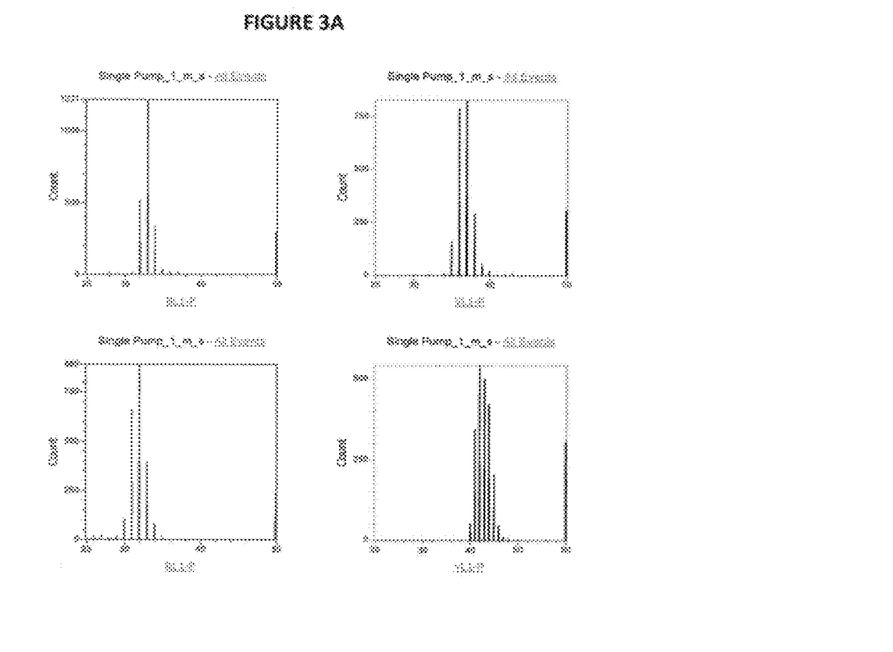
Figure 3B:
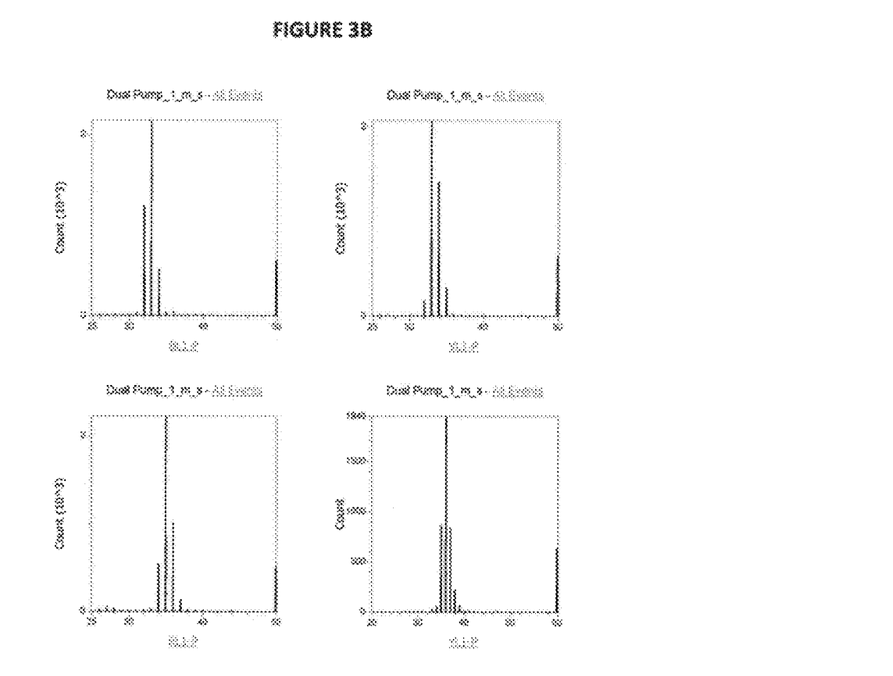

In some or all of the described embodiments, a measurement of about a 2% maximum velocity variation is considered a minute level of pulsatility that is acceptable in most applications. This corresponds to a maximum a span of about 15 points of detected pulse width in the particle arrival distribution parameter (e.g. peak time) at the farthest downstream point of interrogation (e.g. at the yellow laser, FIGS. 3A and 3B as well as FIGS. 4A and 4B, graph YL) from an initial point of interrogation (e.g. at the blue laser FIGS. 3A and 3B as well as FIGS. 4A and 4B, graph BL) point of interrogation. For example, as represented in FIGS. 3A and 3B as well as FIGS. 4A and 4B the blue laser (BL) may be positioned farthest upstream and used to start the clock used to measure arrival times. The violet laser (VL) and red laser (RL) may be positioned close to the blue laser (e.g. 1 space away) and thus the degree of variation from the blue laser is typically small. Continuing with the present example, the yellow laser (YL) is comparatively further away from the blue laser (e.g. at least two spots away) and exhibits the largest difference in the measure of the pulsatility as demonstrated in FIGS. 3A and 3B as well as FIGS. 4A and 4B. Additional examples of using detected pulse width and a particle arrival distribution parameter to measure pulsatility are described in U.S. patent application Ser. No. 14/612,820 incorporated by reference above.

In the embodiments described herein, the measure of pulsatility provided by pumps 155 and 155' is dependent, at least in part, upon the flow rate below which a given single pump produces unacceptable pulsatility. FIGS. 3A and 3B illustrate pulsatility measurements taken using a total forward flow rate of 1 m/s where the data in FIG. 3A illustrates data from a single pump mode of operation, and the data in FIG. 3B illustrates data from a dual pump mode of operation. Each of FIGS. 3A and 3B include 4 graphical representations of data each obtained from emissions in response to excitation one of the laser sources (e.g. BL=blue laser; VL=violet laser; RL=red laser; and YL=yellow laser). For these examples, particles are first interrogated at the blue laser and the yellow laser is farthest downstream from this laser. As a result, the distribution of arrival times is greatest at the yellow laser. In the present example, the variation seen associated with the blue laser is generally attributable to "jitter" in the clock. As described above each graphical representation includes a distribution of points of detected arrival times and when the corresponding graphical representation from 3A is compared to 3B (e.g. blue laser to blue laser, etc.) it is evident that there is generally a tighter distribution (e.g. fewer points across the distribution) of detected pulse width for each graphical representation in FIG. 3B derived from the dual pump mode of operation. The tighter distribution of detected points corresponds to a lower degree of pulsatility as measured by reduced variation in arrival time of particles relative to the respective laser interrogation point. Stated simply, the tighter distribution represents less variation in the velocity of interrogated particles.

Figure 4A:
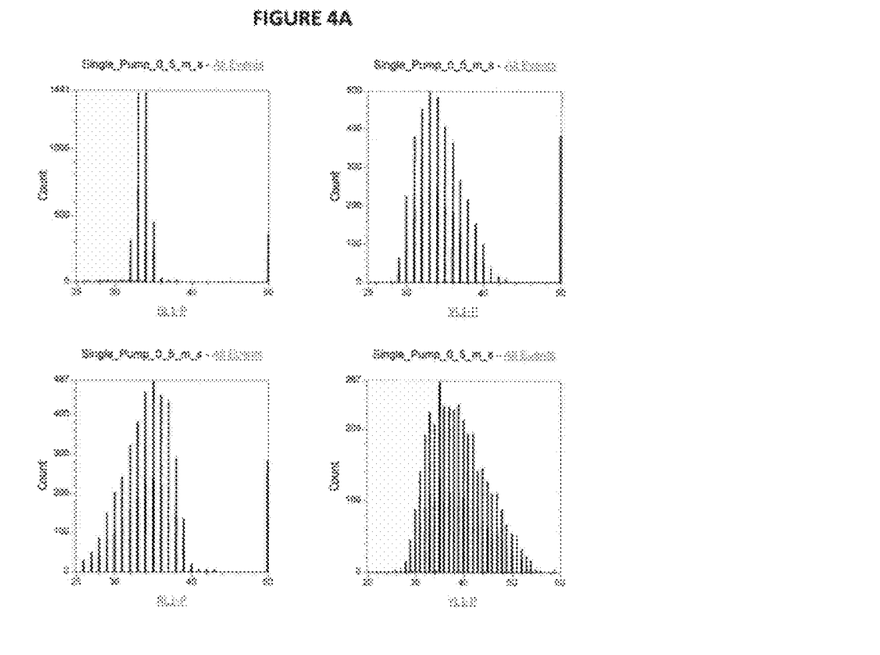
FIGS. 4A and 4B are simplified graphical representations of measured pulsatility using 4 laser sources at a 0.5 m/s flow rate Like reference numerals refer to corresponding parts throughout the several views of the drawings.
Figure 4B:
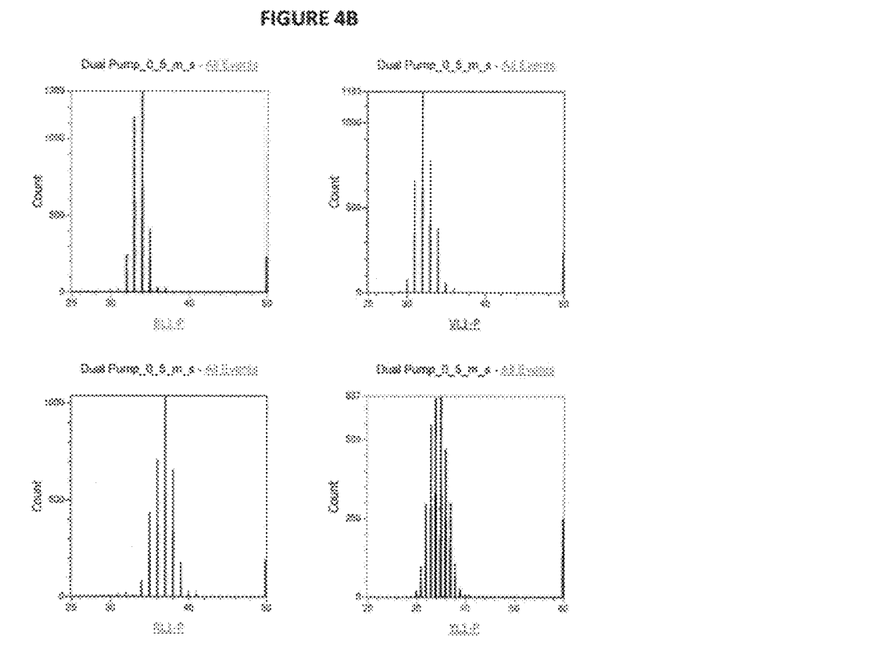

Similar to FIGS. 3A and 3B, FIGS. 4A and 4B illustrate pulsatility measurements taken using a total forward flow rate of 0.5 m/s where the data in FIG. 4A illustrates data from a single pump mode of operation and the data in FIG. 4B illustrates data from a dual pump mode of operation. As with FIGS. 3A and 3B, comparison of the graphical representations in FIGS. 4A and 4B illustrate more pronounced reduction in variation of arrival times (i.e. tighter distribution) for each graphical representation derived from the dual pump mode of operation. In this case a reduction of about 5 fold. FIGS. 4A and 4B illustrate that the dual pump mode of operation provides a stable total forward flow rate with a low measure of pulsatility whereas the single pump must operate at a slower revolution rate that is highly pulsatile. It is notable that in the 0.5 m/s flow rate embodiments illustrated in FIGS. 4A and 4B the pulsatility seen using the violet laser and red laser is significantly reduced from FIG. 4A to be about the same as the baseline jitter in FIG. 4B. In some embodiments, the dual pump mode of operation may provide a stable total forward flow velocity down to about 1 cm/s. For the flow cell dimensions used in FIGS. 3A and 3B as well as 4A and 4B (e.g. 210 µm long×210 µm wide square flow cell dimension), this corresponds to an overall volumetric output of ~10 µl/min. For these examples, the revolution rate for both forward and reverse pumps is higher than what is required for the single pump example at 1 m/s. Also, in the examples provided the velocity of the fluid flow through the flow cell (e.g. typically measured in units of distance/time) is the important aspect as it is what directly affects particles and how the measures of pulsatility are taken.

In the 1 m/s flow rate example given in FIGS. 3A and 3B, the particular pump used has an acceptable measure pulsatility for the single pump configuration as shown in FIG. 3A, even though the pulsatility of the dual pump configuration is significantly better as shown in FIG. 3B. For this same pump at the 0.5 m/s flow rate, however, the measure of pulsatility in the single pump configuration is unacceptable as shown in FIG. 4A relative to the dual pump configuration shown in FIG. 4B.

Continuing the example from above, the "reverse" flow from pump 155' feeds back through junction 210 to pump 155 or can flow into fluid reservoir 205 so that overall sheath fluid consumption is only forward flow rate minus the reverse flow rate. Both pumps are run fast enough so that each by itself has low pulsatility in the respective flow rate. Pump 155' may also dampen the frequency pulses from pump 155 and the fluid is recycled, where a net outflow (pump 155-pump 155') can include a range as low as 10-100 µl/min.

Also illustrated in FIG. 2 is a mode of operation where pumps 155 and 155' are run in the same forward direction, which allows combining the output of the pumps for sheath flow rates that are double or more what a single embodiment of pump 155 can produce. Again, both pumps are run fast enough so that each by itself has a low measure of pulsatility in the flow rate. The architecture and mode illustrated in FIG. 2 produces a high dynamic range of stable sheath flow rate enabling both fast and slow flow rate applications with a high degree of control across the whole range of flow rate. In some embodiments either of pumps 155 and 155' may provide no fluid flow at all or a reverse flow as described above, to produce a desired flow rate with a minute measure of pulsatility. Because pumps 155 and 155' are independently adjustable the flow rate of each may be set by computer 110 or other processor element to provide very precise control of the combined output flow rate where when pumps 155 and 155' are operated at or near their maximum flow rate output the combined output flow rate is fast. Thus, the embodiments described herein provide a wide dynamic range of flow rate with high precision of control not achievable in a single pump format. It will be appreciated that pumps 155 and 155' may both include gear pumps. However combinations of larger and smaller toothed versions may be desirable for sheath delivery when targeting a higher output range of flow rate but with greater adjustment precision. Further, when inlet pumps 155 and 155' are gear pumps that are operated at a high RPM the result is a substantially reduced level of pulsatility relative to the level of pulsatility produced when operated at a low RPM rate and thus the flow rate is considered stable.

As in the example of FIG. 2, junctions 210, 210', 210", and 210''' may include "3-port" junctions or other similar type of junction known in the art. In addition, sample 120 is introduced via sample input 220 into the flow of fluid from junction 210' and may or may not include a fluid flowing at a different flow rate. For example, sample 120 may be introduced with a fluid that forms the "core" diameter portion of a flow of the total fluid flow entering flow cell 160 with the flow from junction 210' becoming the "sheath" portion of a flow that substantially surrounds the core diameter portion of a flow in the dimension of the channel. Those of ordinary skill in the related art appreciate that core diameter dimension depends upon the dimensions of the flow cell, rate of sample fluid flow and rate of sheath fluid flow (e.g. also known as hydrodynamic focusing). Generally, the ratio of dimension of sheath fluid to sample fluid can include a ratio of 1:1 upwards to 1000:1 or more.

Continuing the example from above, the flow rate of a fluid associated with sample 120 may combine with the flow rate exiting junction 210', or alternatively the channel may be dimensioned from the junction where the flow exiting junction 210' meets a flow of fluid comprising sample 120 to flow cell 160 so that the combined fluids do not change the flow rate of the fluid exiting junction 210' or changes the flow rate to a desired flow rate for the fluids to pass through flow cell 160.

Also illustrated in FIG. 2 are outlet pumps 255 and 255' that may include the same or different pump type than pumps 155 and 155'. Alternatively, outlet pumps 255 and 255' may include other pump types or devices that provide a positive and/or negative pressure to the fluid flow. For example, outlet pumps 255 and 255' could include a vacuum reservoir or other type of reservoir that provides a pressure differential. In one mode of operation, the fluid exiting from flow cell 160 passes through junction 210" to outlet pump 255 and junction 210''' to waste 260 or to outlet pump 255' that provides flow in the direction to junction 210". In another mode of operation outlet pump 255" provides a direction of flow such that the fluid exiting from flow cell 160 passes through junction 210" to outlet pumps 255 and 255' to junction 210''' to waste 260 where the overall flow rate to waste 260 is the combined flow rates from pumps 255 and 255'.

Also, the configurations illustrated in FIG. 2 have the very desirable features of providing continuous volumetric delivery of sample 120 from sample input 220 without the need to use an active pumping mechanism such as an external pressure source (pressure based system) or a sample loop source (syringe based system). For example, sample 120 can be drawn from sample input 220 into flow cell 160 by increasing the flow rate of waste output leaving flow cell 160 via output pump 255 and/or 255' to a rate that is above the flow rate leaving junction 210'. The increased flow rate generated by output pump 255 and/or 255' results in a negative pressure that draws a fluid with sample 120 from sample inlet 220 so that the combined fluids from junction 210' and sample inlet 220 flow at the desired flow rate through flow cell 160.

In embodiments of pumps 255 and 255' that have gear elements with small teeth, it may be important to protect pumps 255 and 255' from particles which may clog the small teeth. In some embodiments, use of a larger toothed gear pump for pump 255 or 255' can overcome clogging issues, but the pulsatility increases especially at low flow rates as the dimension of the gear teeth increases can create problems. Also, the use of a pressure differential type reservoir can overcome issues with clogging.

In the same or alternative embodiments, a solution that provides a minute measure of pulsatility can include use of two outlet pumps, such as outlet pumps 255 and 255'. For example, outlet pump 255 that may include a larger tooth gear pump that outputs a high flow rate with decreased pulsatility by running at a high RPM rate and using outlet pump 255' to provide a flow of fluid in the opposite direction (e.g. drawing fluid from junction 210''') to the direction of flow for outlet pump 255. Both pumps 255 and 255' can have larger teeth but a smaller toothed pump can be used as pump 255' for the reverse direction if a clean or filtered supply of fluid is used.

It will be appreciated that the operation of pumps 155, 155', 255, and 255' may be controlled by a controller element associated with flow cytometer 150 or may receive instruction from instrument control software associated with computer 110. It will also be appreciated that the modes of operation of pumps 155-155', and 255-255' depicted in FIG. 2 are illustrative and not mutually exclusive of each other. For example, the mode of operation of input pumps 155-155' for slow flow rate operation (e.g. input pump 155' providing a flow in an opposite direction to the flow provided by input pump 155) may be used with the mode of operation of output pumps 255-255' for reduced clogging (e.g. output pump 255' providing a flow in an opposite direction to the flow provided by input pump 255).

In the described embodiments, flow rates can be calculated volumetrically using counted revolutions and volume per revolution of the associated gear pumps. In some embodiments it may also be desirable to include pressure sensor 230 that can be employed to measure the differential pressure between the flow entering and the flow exiting flow cell 160. Those of ordinary skill in the related art appreciate that a differential pressure measurement includes a comparison of a first pressure value to a second pressure value to calculate the difference between the two (e.g. can include a pressure value that is the difference between the two that may also be a positive or negative value if one of the pressure values is used as a relative reference for the other). In the described embodiments one of the pressure values is provided by pressure sensor 230 and the second pressure value may be provided by a second implementation of pressure sensor 230, or by using a pressure value associated with the ambient air pressure in the environment or from a known input pressure (e.g. provided by pumps 155, 155', 255, 255', vacuum reservoirs, or other pressure input sources). It is also generally appreciated that pressure sensors typically measure the pressure of a fluid, usually stated in terms of force per unit area. The measurement of differential pressure may be used, among other things, to compute the flow rate of the fluid using the dimensional characteristics of the fluidic components and characteristics of the fluids (e.g. viscosity). Alternatively, the measured differential pressure value may be used to determine one or more characteristics of the fluid such as the viscosity which may be particularly useful with applications that utilize oils in the flow.

In other embodiments, the combination of pressure sensor 230 and revolution speed control of pumps 155, 155', 255, or 255' can be used to volumetrically control input flow rates of sample 120 via closed loop feedback. If, for example, pressure is applied via a sample reservoir to sample input 220 and one or embodiments of pressure sensor 230 are set to measure absolute pressure just prior to flow cell 160 and differential pressure from the sample reservoir to sample input 220 prior to flow cell 160, then sample 120 will begin to be delivered when differential pressure is just above 0. By then adjusting RPM rate of one or more of pumps 155, 155', 255, or 255' and optionally increasing absolute pressure at the sample reservoir such that absolute pressure just prior to flow cell 160 is constant, the volumetric flow rate of sample 120 will approximately correspond to the change in volumetric delivery of fluid by pumps 155, 155', 255, or 255' as measured by the changes in RPM rate.

FIG. 2 provides an illustrative example of pressure sensor 230 positioned to measure the flow pressure exiting flow cell 160, however it will be appreciated that pressure sensor 230 may also be positioned to measure the flow pressure entering flow cell 160. Further, in some embodiments there may be an implementation of pressure sensor 230 positioned to measure the flow pressure at both the entrance and exit to flow cell 160. For example, if the total forward flow rate of pumps 155/155' matches the total forward flow rate of pumps 255/255' then the differential pressure would be about zero. If the expected total forward flow rates do not match (e.g. expected based on number of revolutions of pumps 155/155' and 255/255' for desired output flow rates) then there is an indication that there is a problem in the system. The problems could include a problem with the gear pumps such as clogging or end of life, or problems in the fluidic network which could include clogging of a channel or valve. In the described example, various components can be isolated (e.g. by adjusting pump output and/or direction) and tested using the differential pressure measurement to find the specific issue.

Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiments.

What is claimed is:

1. A system with a minute measure of pulsatility in a flow of a fluid, comprising:
a first pump configured to flow the fluid from a first junction to a second junction at a first flow rate that comprises a measure of pulsatility; and
a second pump configured to flow a portion of the fluid from the second junction to the first junction at a second flow rate that is less than the first flow rate to produce a forward flow of the fluid at a third flow rate from the second junction with a minute measure of pulsatility, wherein the first pump, first junction, second junction, and second pump define a fluidic circuit wherein the fluid is flowed at the first flow rate in a first fluid pathway between the first junction and the second junction and wherein the fluid is flowed at the second flow rate in a second fluid pathway between the second junction and the first junction.

2. The system of claim 1 wherein the second flow rate is slower than the first flow rate.

3. The system of claim 1 wherein the first pump comprises a gear pump.

4. The system of claim 3 wherein the first pump comprises small teeth.

5. The system of claim 3 wherein the first pump operates at 1000RPM.

6. The system of claim 3 wherein the second pump comprises a gear pump.

7. The system of claim 5 the first pump comprises small teeth.

8. The system of claim 3 wherein the second pump operates at 990RPM.

9. The system of claim 1 wherein the first flow rate and the second flow rate are adjustable.

10. The system of claim 1 wherein the fluid flowing at the third flow rate enters a detection region.

11. The system of claim 10 wherein the detection region comprises a flow cell.

12. The system of claim 1 wherein a sample fluid is introduced to the fluid flowing at the third flow rate.

13. The system of claim 12 wherein the sample fluid and the fluid flowing at the third flow rate combine and become a single flow, wherein the sample fluid forms a core diameter portion of the single flow and the fluid flowing at the third flow rate comprises a sheath portion of the single flow.

14. The system of claim 13 wherein the single flow flows at a fourth flow rate.

15. The system of claim 14 wherein a third pump produces the fourth flow rate that is greater than the third flow rate, wherein the third pump draws the sample fluid into the fluid flowing at the third flow rate.

16. A method for providing a fluid flow with a minute measure of pulsatility, comprising:
while flowing a fluid in a first fluid pathway from a first junction to a second junction at a first flow rate that comprises a measure of pulsatility,
flowing a portion of the fluid in a second fluid pathway from the second junction to the first junction at a second flow rate that is less than the first flow rate to produce a forward flow at a third flow rate of the fluid from the second junction with a minute measure of pulsatility.

17. The method of claim 16 wherein the fluid flowing at the third flow rate enters a detection region.

18. The method of claim 16 wherein a sample fluid is introduced to the fluid flowing at the third flow rate.

19. The method of claim 18, wherein the sample fluid and the fluid flowing at the third flow rate combine and become a single flow, wherein the sample fluid forms a core diameter portion of the single flow and the fluid flowing at the third flow rate comprises a sheath portion of the single flow.

20. The method of claim 19 wherein the single flow flows at a fourth flow rate.

21. The system of claim 1, wherein the first pump is disposed in the first fluid pathway between the first junction and the second junction.

22. The system of claim 1, wherein second pump is disposed in the second fluid pathway between the second junction and the first junction.

23. The method of claim 16, wherein the first pump is disposed in the first fluid pathway between the first junction and the second junction.

24. The method of claim 16, wherein second pump is disposed in the second fluid pathway between the second junction and the first junction.

* * * * *